United States Patent [19]

Nandagiri et al.

[11] Patent Number: 5,362,487
[45] Date of Patent: * Nov. 8, 1994

[54] CYSTEAMINE PERMANENT WAVE COMPOSITION AND METHOD

[75] Inventors: Arun Nandagiri, Libertyville; Richard A. Abbott, Westmont; Renee E. Nardone, Chicago, all of Ill.; Edward T. Borish, Mahwah, N.J.

[73] Assignee: Helene Curtis, Inc., Chicago, Ill.

[*] Notice: The portion of the term of this patent subsequent to Nov. 9, 2010 has been disclaimed.

[21] Appl. No.: 111,305

[22] Filed: Aug. 24, 1993

Related U.S. Application Data

[63] Continuation-in-part of Ser. No. 819,113, Jan. 10, 1992, Pat. No. 5,260,054.

[51] Int. Cl.$^5$ .......................... A61K 7/06; A61K 7/09; A61K 7/11
[52] U.S. Cl. .......................... 424/71; 424/72; 132/223
[58] Field of Search .......................... 424/70, 71, 72; 132/223

[56] References Cited

U.S. PATENT DOCUMENTS 2,577,710 12/1951 McDonough .......................... 133/7
2,577,711 12/1951 McDonough .......................... 132/7
5,208,014 5/1993 Dubief et al. .......................... 424/71

FOREIGN PATENT DOCUMENTS 2053714A of 0000 Japan .

OTHER PUBLICATIONS

German Offen. DE 3,631,991 (See CA Selects: Cosmetic Chemicals, Issue 1, 1989, 109:236730h).

Primary Examiner—Thurman K. Page
Assistant Examiner—Carlos Azpuru
Attorney, Agent, or Firm—Marshall, O'Toole, Gerstein, Murray & Borun

[57] ABSTRACT

A single formula, mild permanent wave reducing composition and method of permanently waving or reshaping human hair that provides a strong, long lasting curl and leaves the hair soft while minimizing further damage to already damaged hair. The composition contains a cysteamine reducing agent compound selected from the group consisting of cysteamine, a cysteamine salt, and mixtures thereof; and a second reducing agent selected from the group consisting of a monothioglycolate; an alkanolamine salt of thioglycolic acid; a thiolactic acid; a thioglycolic acid; thioglycerin; salts of thiolactic acid; cysteine; a salt of cysteine; a sulfite; a hyposulfite; and a bisulfite. The cysteamine compound should be present in an amount of about 7.8% to about 9% by weight; and sufficient additional alkali, if necessary, to bring the pH of the composition to about 7.8 to about 8.8. Unexpectedly, the composition is applied to any type of hair, regardless of structural damage to the hair, resulting in the same degree of curl tightness and softness and can be applied much more frequently than prior art permanent wave compositions without significant damage to the hair.

11 Claims, 5 Drawing Sheets

CYSTEAMINE PERMANENT WAVE COMPOSITION AND METHOD

CROSS REFERENCE TO RELATED APPLICATION

This application is a continuation-in-part of co-pending U.S. application Ser. No. 07/819,113 filed Jan. 10, 1992, now U.S. Pat. No. 5,260,054, which is hereby incorporated by reference.

FIELD OF THE INVENTION

The present invention is directed to a permanent wave lotion composition containing a combination of reducing agents, including cysteamine, and method for relatively permanently reshaping or curling human hair into a lasting curl pattern. More particularly, the present invention is directed to a composition and method capable of forming a "permanent" wave in human hair such that regardless of the condition of the hair, i.e., whether it be substantially undamaged or normal hair, tinted hair, frosted hair, bleached hair or hair substantially damaged as a result of some other prior hair treatment or environmental condition, the composition will permanently reshape both normal and damaged hair to substantially the same extent without the danger of overprocessing. Significantly, the composition does not require a compound added for the purpose of establishing an equilibrium reaction with the reducing agent, e.g., a dithioglycolate, such as diammonium dithioglycolate, to prevent overprocessing of and damage to the hair. Further, the composition can be applied repeatedly to the hair without significant damage so that the hair can be permed at least every 3 to 6 weeks to maintain a fresh looking perm without significant damage.

BACKGROUND OF THE INVENTION

In general, permanent waving of human hair is achieved by chemically breaking the sulfur to sulfur or disulfide cystine bonds occurring naturally in human hair and then reforming the cystine bonds while the hair is wrapped or curled on rods. The sulfur to sulfur cystine bonds in human hair maintain the hair in a naturally straight or curly configuration and, in order to permanently reshape the hair into a lasting, different configuration, a significant percentage of the sulfur to sulfur bonds must be broken and then reestablished after the hair is reconfigured in a desired position, such as wrapped around a suitable mandrel or roller. In general, the sulfur to sulfur cystine bonds are broken with a composition containing a reducing agent and after the hair is wound into a curl formation around a rod or roller, the sulfur to sulfur cystine bonds are relinked or reestablished while the hair is in the curl formation by contacting the hair in the new formation with an oxidizing agent, such as hydrogen peroxide or a water-soluble bromate.

As set forth in German Offen. DE 3,631,991, others have used a reducing agent composition that is a combination of cysteamine, or its salts, together with a monothioglycolic acid ester for permanent hair waving (see CA Selects: Cosmetic Chemicals, Issue 1, 1989, 109: 236730h). Also an N-acylcysteamine $HSCH_2CH_2NHCOR$-(R=2-10 C alkyl), as a hair reducing compound, has been used together with another reducing agent selected from the group consisting of cysteine, acidic sodium hyposulfite, sodium sulfite, thioglycerol and thiolactic acid, as disclosed in Japanese Patent JP63146808. Similarly, published European Patent Application 88306449.5, publication number 0299764, discloses the use of cysteamine as a reducing agent together with sulfite, bisulfite and disulfide compounds, such as cystamine, to effect reoxidation. The use of cystamine, as an oxidizing agent in the permanent waving process, is disclosed in Siuta-Mangano U.S. Pat. No. 4,795,629. Japanese published Patent Application No. 2053-714-A discloses cysteamine together with a dithioglycolate stop action compound. These patents and publications, however, do not recognize the use of cysteamine as a reducing agent in the concentration and at the pH disclosed herein, or that cysteamine alone, or in combination with one or more additional reducing agents, at the cysteamine concentration and pH ranges disclosed herein, provides an essentially constant aggressivity with time.

The reducing action of mercaptans on keratin is due mostly to the dissociated form of the thiol groups, the thiolate anion. Acid permanent waves sufficiently curl hair at a lower pH compared to alkaline permanents because the waving agents in these permanents have low pKa values and thus exist predominantly in dissociated (thiolate) form at a pH near neutral, or slightly acidic pH. Hence, the pKa value shows that some mercaptans are efficient at high pH while others with a low pKa value and high ionization constant are efficient at lower pH values. For example, it is well known that the alkaline salts of thioglycolic acid, e.g., the ammonium salt of thioglycolic acid (pKa=10.4) has acceptable waving efficiency only if the pH of solution exceeds 9, see Zviak, Charles, The Science of Hair Care, Permanent Waving and Hair Straightening, p. 191, 1986; while amides such as thioglycolamide (pKa=8.4), and esters such as glycerol thioglycolate (pKa=7.8) give acceptable waving efficiency at neutral and even slightly acid pH.

The cysteamine-based reducing agent containing composition and method of the present invention includes a second reducing agent compound selected from the group consisting of a monothioglycolate; an alkanolamine salt of thioglycolic acid; a thiolactic acid; a thioglycolic acid; thioglycerin; salts of thiolactic acid; cysteine; a salt of cysteine; a sulfite; a hyposulfite; and a bisulfite, and is unexpectedly effective in the pH range of about 7.8 to about 8.8 and particularly in the pH range of about 8 to 8.5, without increasing hair damage or otherwise adversely affecting the benefits of a cysteamine reducing agent within the aforementioned pH and concentration ranges.

Different reducing agents are effective to break the cystine bonds that cross link human hair protein at the different pHs. Generally speaking, the acid permanent wave compositions having a lower pH include reducing agents such as bisulfites, e.g., ammonium bisulfite, or glycerol monothioglycolate, capable of breaking the sulfur to sulfur cystine bonds within lower pH ranges, whereas the alkaline permanent wave compositions, having pHs in the range of about 7.5 to 9.5, require an alkaline salt of thioglycolic acid—so that the alkali can penetrate and swell the hair shaft for easier penetration of the reducing agent in order to break the sulfur to sulfur cystine bonds.

The use of diammonium dithiodiglycolate in acid or alkaline permanent wave lotions allows greater flexibility in processing time because it minimizes the possibility of overprocessing. This is due to the fact that the reaction of thioglycolic acid (TGA) with hair keratin is an equilibrium process. Thus by including diammonium dithiodiglycolate (oxidized TGA) in the wave lotion, the rate of the reaction of the thioglycolic acid with hair keratin is decreased and prevented from going to completion.

Generally, the permanent wave compositions of the prior art do not include moisturizers, such as glycerins, since moisturizers cause loss of curl, as disclosed in Cannell et. al. U.S. Pat. No. 4,301,820.

One of the biggest problems associated with the permanent waving process is due to human error in the person applying the permanent waving lotion. If the reducing agent is applied to the hair shaft for the wrong period of time, too many or too few of the sulfur to sulfur bonds in the hair shaft are broken, resulting in seriously damaged hair or resulting in hair which has not been sufficiently treated to achieve a permanent wave with long lasting potential. Some of the reasons that the person applying the permanent wave composition has difficulty in determining the correct amount of time for processing is that the reducing agent reaction in breaking the sulfur to sulfur bonds is dependent upon the amount of heat applied to the hair; the amount of time the reducing agent is in contact with the hair; the concentration of reducing agent; the pH of the lotion applied; and the condition of hair.

Perhaps the most difficult factor for the applier of the permanent wave lotion to assess in determining how long to apply the reducing agent to the hair is the condition of the hair at the time of the permanent wave. It is well documented in the literature and prior art that the hair can be damaged by abuse of chemicals, e.g., by shampooing, permanent waving, tinting, frosting, bleaching, and particularly any hair treatment involving the use of hydrogen peroxide; mechanical treatment, e.g., thermal appliances; and environmental conditions, e.g., climate and pollution. It is well known that damaged hair, depending upon the stage and degree of damage of the hair, has significantly different chemical activity to reducing agents than normal or undamaged hair. If too many of the sulfur to sulfur bonds in the hair are broken by the reducing agent, the hair will be seriously weakened and may disintegrate.

It is theorized that somewhere in the range of about 20% to about 60% of the natural sulfur to sulfur cystine bonds in the hair shafts should be broken in order to give the hair the capability of being reshaped to any desired shape, such as curled around a rod or roller, and capable of retaining this shape. If too few of the sulfur to sulfur bonds are broken, the natural or normal configuration of the hair will predominate, causing the hair to retain its previous shape. This is because the predominant prior or natural bonds in the hair dictate that the hair will remain in the old configuration or shape. Hydrogen bonds are physically broken when wet hair is stretched and wrapped around a roller. When the hair is dried, the hydrogen bonds are reformed in a curled position or shape. While the hydrogen bonds aid to maintain the hair in the new configuration, the sulfur to sulfur cystine bonds are much stronger and, to a much greater extent than the hydrogen bonds, control the efficacy of the permanent wave.

In order to successfully provide a satisfactory permanent wave in the hair, the sulfur to sulfur cystine bonds reformed in the hair in the new or curled configuration, when the hair is later oxidized with the neutralizing agent, should be stronger than the prior or natural cystine hair bonds. It is desired, therefore, when permanent waving, that enough new bonds in a new hair configuration are formed during permanent waving to outweigh the number of old bonds remaining that tend to form the hair in its prior or natural configuration, whether it be straight or naturally curled.

Since damaged hair already has a significant number of the sulfur to sulfur cystine bonds broken due to some chemical, mechanical or environmental abuse, particularly the chemical abuses, such as bleaching, tinting or frosting, it is difficult to determine what length of time, and what reducing agent concentration to apply to the hair to provide the hair with the proper number of sulfur to sulfur bonds remaining after the reducing agent treatment. Significantly damaged hair, such as tinted hair, may require a reducing agent lotion application for a period of only about 5 minutes whereas a normal hair, not significantly damaged, may require the reducing agent lotion for a period of approximately 20 minutes under the same reducing agent concentration and temperature in order to result in both the damaged and normal hair having approximately the same curl configuration. Ideally, after the reducing agent treatment, every one of the hair shafts treated will contain the same ratio of broken to unbroken bonds so that this same ratio can be re-established in each hair shaft when the hair is in the new configuration to provide a consistent strong curl over the entire head of hair.

Generally, the reducing agent lotion is applied to the hair by first shampooing the hair and then applying the reducing agent lotion to the hair, either before or after the hair is wrapped around suitable rollers. Since it is not possible for even the experienced permanent wave applier to accurately determine visually the extent of damage to the hair in order to have a better idea of how long the reducing agent should be in contact with the hair, it is necessary to take a "test curl" so that after a predetermined amount of time, for example 10 minutes, a first roller is removed from the hair and the curl is felt and stretched in an attempt to determine if the curl formation is strong enough. Once it is determined that the reducing agent has been in contact with the hair for a sufficient time period, the hair is rinsed thoroughly with water while still on the rollers or rods and, while the hair remains on the rollers or rods, a neutralizing agent is applied to oxidize and reform the sulfur to sulfur bonds while the hair is in the new, rolled configuration. The neutralizing agent contains an oxidizing agent, such as hydrogen peroxide or a bromate salt, in order to reestablish the sulfur to sulfur bonds to leave the hair in a relatively permanent, e.g., 2-4 months, new configuration. The rods are removed, before or after rinsing out the neutralizing agent.

When the reducing agent lotion is applied to sections of the head prior to rolling that portion of the hair onto the rods it is called a lotion wrap whereas when the hair is rolled on the rods or rollers first and then the lotion applied onto all of the hair after rolling, this is called a water wrap. The timing for the reducing agent to be in contact with the hair for a lotion wrap is begun from the time that all rods are on the head, and the timing for a water wrap begins from the time that the lotion application is completed. The capability of using a water wrap is clearly more desirable since the lotion is applied to the entire head of hair all at once in a short period of time and can be rinsed from the hair all at once to provide a more uniform reducing agent contact time for all of the hair.

Other prior art patents directed to permanent waving compositions intended to permanently wave both normal and damaged hair are found in the Klemm et. al. U.S. Pat. No. 4,273,143; and Cannel et. al. U.S. Pat. No. 4,301,820. Japanese Patent No. 57-212110 appears to be directed to a post-permanent treatment containing glycerine to give hair sheen and luster.

Japanese published application Nc. 55-136857 teaches that cysteamine-based permanent waving compositions are more effective with thioglycolic acid reducing agents, but does not disclose the cysteamine pH and concentration of the present invention, or the essentially constant aggressivity disclosed herein.

In accordance with the present invention, a cysteamine-based permanent wave composition, containing a thioglycolate or thioglycolic acid, is provided in a single formula which can be applied in a single predetermined amount of time to the hair, regardless of the structure of the hair, whether it be damaged or not, and this composition is capable of being water wrapped or lotion wrapped without the use of a dryer, hair caps or other heat treatment to speed the reducing agent action.

Prior art alkaline compositions containing a salt of thioglycolic acid as a reducing agent are known to produce a tight curl but leave the hair feeling harsh due to the high alkalinity content. Prior art acid wave compositions containing glycerol monothioglycolate as a reducing agent require the mixing of the reducing agent into a separate lotion immediately prior to use since glycerol monothioglycolate will hydrolyze in contact with water and, therefore, must be kept separate until immediately prior to use. Further, the acid wave compositions generally require heat to help swell the hair for reaction with the reducing agent since the hair is not normally swelled sufficiently at the low pH of the acid wave compositions. The cysteamine-based reducing agent compositions of the present invention include a second reducing agent compound selected from the group consisting of a monothioglycolate; an alkanolamine salt of thioglycolic acid; a thiolactic acid; a thioglycolic acid; thioglycerin; salts of thiolactic acid; cysteine; a salt of cysteine; a sulfite; a hyposulfite; and a bisulfite. The preferred second reducing agent is a monothioglycolate, such as ammonium thioglycolate (ATG), or an alkanolamine salt of thioglycolic acid, such as monoethanolamine thioglycolate. The cysteamine-based reducing agent-containing permanent wave compositions of the present invention solve the above mentioned prior art deficiencies while being capable of effective permanent waving on hair, regardless of its extent of damage and regardless of the amount of time that the reducing agent composition (waving lotion) is left in contact with the hair.

SUMMARY OF THE INVENTION

In accordance with the present invention, the performance of a cysteamine-based reducing agent formulation is further improved by the addition of a second reducing agent, particularly ammonium thioglycolate (ATG), without increasing hair damage or otherwise adversely effecting the benefits previously seen with cysteamine formulations.

Cysteamine has been shown to provide good curl and leave hair in excellent condition when pH and concentration are tightly controlled. Attempts to increase curl formation by raising the pH or concentration of cysteamine did not yield successful results because cysteamine exhibits a peak effect at a pH of 8.3 and a concentration of 8.3% by weight. At this concentration and pH, cysteamine formulations were shown to be non-damaging to hair and the aggressivity of the lotion did not change appreciably over time, giving the hair stylist more flexibility on processing time.

In brief, the present invention is directed to a single formula, mild permanent wave reducing composition and method of permanently waving or reshaping human hair that provides a strong, long lasting curl, and leaves the hair soft, while minimizing further damage to already damaged hair. Generally, the composition contains a cysteamine reducing agent compound selected from the group consisting of cysteamine; a cysteamine salt, e.g., cysteamine hydrochloride, cysteamine chlorohydrate, cysteamine acetate, cysteamine phosphate, cysteamine nitrate, cysteamine bromide or cysteamine fluoride; and mixtures thereof; a second reducing agent selected from the group consisting of a monothioglycolate; an alkanolamine salt of thioglycolic acid; a thiolactic acid; a thioglycolic acid; thioglycerin; salts of thiolactic acid; cysteine; a salt of cysteine; a sulfite, a hyposulfite; and a bisulfite. In the preferred embodiment, the cysteamine compound should be present in an amount of about 7.8% to about 9%, preferably about 7.8% to about 8.8% by weight; the second reducing agent can be included in an amount in the range of about 0.1% to about 18% by weight of the composition; and the reducing agent composition should include sufficient additional alkali, if necessary, to bring the pH of the composition to about 7.8 to about 8.8, preferably about 8 to about 8.5. Optionally, a hair softening and/or moisturizing agent, such as glycerine is included in the composition in an amount of about 0.1% to about 20% by weight, preferably about 0.1% to about 15% by weight of the composition.

This cysteamine-based multiple reducing agent-containing composition is easy to use and apply and includes a second reducing agent, such as a monothioglycolate; an alkanolamine salt of thioglycolic acid; a thiolactic acid; a thioglycolic acid; thioglycerin; salts of thiolactic acid; cysteine; a salt of cysteine; a sulfite; a hyposulfite; and a bisulfite second reducing agent, without damaging the hair while providing a strong, tight curl and leaving the hair unexpectedly soft. The composition can be lotion or water wrapped and can be used with or without heat. Unexpectedly, the composition is applied to any type of hair, regardless of structural damage to the hair, resulting in the same degree of curl tightness and softness and can be applied much more frequently than prior art permanent wave compositions without significant damage to the hair.

Accordingly, an aspect of the present invention is to provide a new and improved permanent wave composition capable of breaking sulfur to sulfur bonds in human hair so that the hair can be reconfigured in a different configuration. The sulfur to sulfur human hair bonds can be reestablished with an oxidizing agent to maintain the new hair configuration for a substantial time period.

Another aspect of the present invention is to provide a new and improved permanent wave lotion containing multiple reducing agents, including a cysteamine reducing agent and a second reducing agent, preferably a monothioglycolate, wherein the multiple reducing agent-containing wave lotion is capable of breaking sulfur to sulfur hair bonds without causing further significant damage to tinted, frosted, bleached or other substantially damaged hair.

Another aspect of the present invention is to provide a new and improved cysteamine-based permanent wave reducing agent composition that includes a second reducing agent, such as a monothioglycolate; an alkanolamine salt of thioglycolic acid; a thiolactic acid; a thioglycolic acid; thioglycerin; salts of thiolactic acid; cysteine; a salt of cysteine; a sulfite; a hyposulfite; and a bisulfite that is capable of breaking sulfur to sulfur human hair bonds leaving normal and damaged hair with approximately the same ratio of broken to unbroken sulfur to sulfur bonds when contacted with the composition for the same time period so that the same degree of curl tightness can be achieved in both normal and damaged hair.

Another aspect of the present invention is to provide a permanent wave reducing agent-containing composition including a hair softening and moisturizing agent that enhances the curl achieved with the composition.

These and other aspects and advantages of the present invention will become apparent from the following detailed description of the preferred embodiment.

DETAILED DESCRIPTION OF THE PREFERRED EMBODIMENT

The present invention is directed to a permanent wave composition capable of permanently waving both damaged and undamaged hair in a single formulation, water-wrap, applied for a constant processing time as a mild permanent that produces a tight, long lasting curl formation and can be applied frequently without significant hair damage. The capability of permanently waving both damaged and undamaged hair repeatedly with a single formulation in a single processing time without requiring a test curl, without causing further damage to the hair, is totally unique in the industry and removes the opportunity for error from the person applying the permanent wave lotion.

The composition of the present invention is a single formula, mild, alkaline permanent wave conditioning composition capable of waving or reshaping human hair and provides a strong, long lasting curl without further damaging already damaged hair. Generally, the composition contains a cysteamine compound selected from the group consisting of cysteamine; a cysteamine salt, such as cysteamine hydrochloride, cysteamine chlorohydrate, cysteamine acetate, cysteamine phosphate, cysteamine nitrate, cysteamine bromide or cysteamine fluoride; and mixtures in an amount of about 7.8% by weight to about 9% by weight, particularly about 8% to about 8.5% by weight; and a second reducing agent, selected from the group consisting of a monothioglycolate; an alkanolamine salt of thioglycolic acid; a thiolactic acid; a thioglycolic acid; thioglycerin; salts of thiolactic acid; cysteine; a salt of cysteine; a sulfite; a hyposulfite; and a bisulfite.

In a preferred embodiment, the waving lotion has a pH in the range of about 8 to about 8.5 and a cysteamine concentration of about 8% to about 8.5% by weight, and particularly about 8.3 for both pH and concentration (% by weight). Preferably, the reducing composition also includes a hair moisturizer and/or softener selected from a polyhydroxyl alkyl compound, a polyalkylene glycol glycerol ether, an ethoxylated fatty alcohol, a fatty alcohol polymerized either, and mixtures thereof in an amount of about 0.1% to about 20% by weight, particularly about 0.1% to about 15% by weight.

Examples of second reducing agents useful in accordance with the present invention are as follows. A monothioglycolate, including the preferred ammonium thioglycolate (ATG), as well as potassium thioglycolate, and sodium thioglycolate. A salt of thiolactic acid, such as ammonium thiolactate. Alkanolamine salts of thioglycolic acid, such as ethanolamine thioglycolate, and methanolamine thioglycolate. These additional (second) reducing agents can be combined within the waving lotion, together with cysteamine, to provide any number of reducing agents, in addition to cysteamine. The total concentration of additional reducing agents, other than cysteamine, should be in the range of about 0.1% to about 18% by weight of the composition. It is preferred that the total concentration of additional reducing agents, other than cysteamine, is in the range of about 1% to about 10% by weight, more preferably about 2% to about 6% by total weight of the waving lotion composition.

Optionally, the composition of the present invention includes a conditioner to improve the combing and manageability of the hair. Particularly, suitable conditions are the polymeric quaternary ammonium salts, such as Polyquaternium 1 through Polyquaternium 14, inclusive, conditioners defined on page 245, CTFA Cosmetic Ingredient Dictionary, Third Edition, 1982, hereby incorporated by reference. The preferred conditioners are Polyquaternium-4, Polyquaternium-10 and Polyquaternium-11. The conditioner, when added, is included in an amount of about 0.01% to about 2% by weight of the composition.

Other common cosmetic additives can be incorporated into the composition of the present invention, as long as the basic properties of the permanent wave composition are not substantially adversely affected. These additives include, but are not limited to, commonly used fragrances, dyes, opacifiers, pearlescing agents, thickeners, foam stabilizers, preservatives, water softening agents, acids, bases, buffers and the like; and will usually be present in weight percentages of less than about 1% each, and about 2% to about 5% in total. The composition vehicle is predominantly water but organic solvents also can be added to the composition in order to solubilize compounds that are not sufficiently soluble in water. Suitable solvents include the lower alcohols, such as ethanol and isopropanol and mixtures. These solvents can be present in the hair setting composition of the present invention in an amount from about 1% to about 75% by weight and in particular from about 5% to about 50% by weight, based on the total weight of the composition.

The composition optionally can be thickened, for example, with sodium alginate, gum arabic, cellulose derivatives such as methylcellulose, hydroxyethylcellulose, hydroxypropylmethylcellulose and carboxymethylcellulose, and various polymeric thickeners, such as acrylic acid derivatives. It is also possible to use inorganic thickeners, such as bentonire. These thickeners, when included, preferably are present in an amount from about 0.1% to about 10% by weight and, in particular, from about 0.5% to about 3% by weight, based on the total weight of the composition.

The composition has a pH in the range of about 7.8 to about 8.8, preferably about 7.8 to about 8.5. To achieve the full advantage of the present invention, the composition has a pH of about 8 to 8.3 for best curl retention when cold waved. This pH can be achieved by the addition of an alkanolamine, ammonia, an ammonium carbonate, or a metal hydroxide to the composition of the present invention.

Moisturizers enhance the curl formation of the permanent wave composition of the present invention. The use of polyhydric alcohols or polyhydroxy alkane compounds, such as ethylene glycol, glycerine, propylene glycol, or polyoxyethylene glyceryl ether in this composition leave the hair in better condition due to humectant properties and surprisingly does not compromise curl formation, but provides the hair with a more uniform and natural curl.

These moisturizers are selected from the group consisting of polyhydroxyalkyl compounds, particularly alkylene glycols and polyalkylene glycols, and especially ethylene glycol and the polyethylene glycols; propylene glycol and the polypropylene glycols; polyethylene glycol glyceryl ethers; ethoxylated fatty alcohols; and fatty alcohol polyglycol ethers. Examples of suitable moisturizers include glycols and triols such as glycerine, ethylene glycol, propylene glycol, 1,3-butylene glycol, 1,2,6-hexanetriol, 1,5-pentanediol, 2-methyl pentanediol-2,4, and 2-ethyl hexanediol-1,3. Further examples of suitable moisturizers include the polyalkylene glycols, such as those compounds having the formula wherein R is H or CH$_3$, and n has an average value of 2 to 600; when R=H, particularly suitable moisturizers have n in the range of 4 to 600; and when R=CH$_3$, particularly suitable moisturizers have n in the range of 2 to 34. The polyalkylene glycols that can be used as moisturizers in the permanent wave composition of the present invention are exemplified by, but not limited to, compounds such as polyethylene glycol 200; polyethylene glycol 400; polyethylene glycol 600; polypropylene glycol 150; tetraethylene glycol; and dipropylene glycol.

Examples of other suitable moisturizers include the polyethylene glycol glyceryl ethers, such as polyethylene glycol 600 glyceryl ether and polyethylene glycol 26 glyceryl ether. Furthermore, the ethoxylated nonyl phenols and ethoxylated octyl phenols, particularly nonoxynol, C$_9$H$_{19}$C$_6$H$_4$(OCH$_2$CH$_2$)$_n$—OH, wherein n averages at least 6 and up to about 100; and octoxynol, C$_8$H$_{17}$S$_6$H$_4$(OCH$_2$CH$_2$)$_n$—OH, wherein n averages at least 7 and up to about 40, also are suitable moisturizers for use in the composition of the present invention. Suitable ethoxylated fatty alcohols for use as moisturizers in the composition of the present invention include compounds having the formula R—(OCH$_2$CH$_2$)$_n$OH, wherein R is an alkyl group containing from about 12 to about 30 carbon atoms and n averages at least 6. In addition, fatty alcohol polyglycol ethers having the formula wherein R is an alkyl group containing from about 8 to about 18 carbon atoms, n=0 to 6, m=0 to 6, and n+m is at least 6, also are useful as moisturizers in the composition of the present invention.

The composition of the present invention is easy to use and apply, repeatedly, without damaging the hair while providing a strong, tight curl and leaving the hair unexpectedly soft. The composition can be lotion or water wrapped and can be used with or without heat. Unexpectedly, the composition is applied to any type of hair, regardless of structure damage to the hair, resulting in the same degree of curl tightness and softness.

It is most surprising in the art that the composition of the present invention is capable of treating both normal and damaged hair, such as tinted hair, in a single formula, using a non-critical processing time for both normal and damaged hair and requires neither a test curl to determine the processing time nor a dryer to fix the processing time while capable of repeated applications without significant hair damage.

Figure 3:
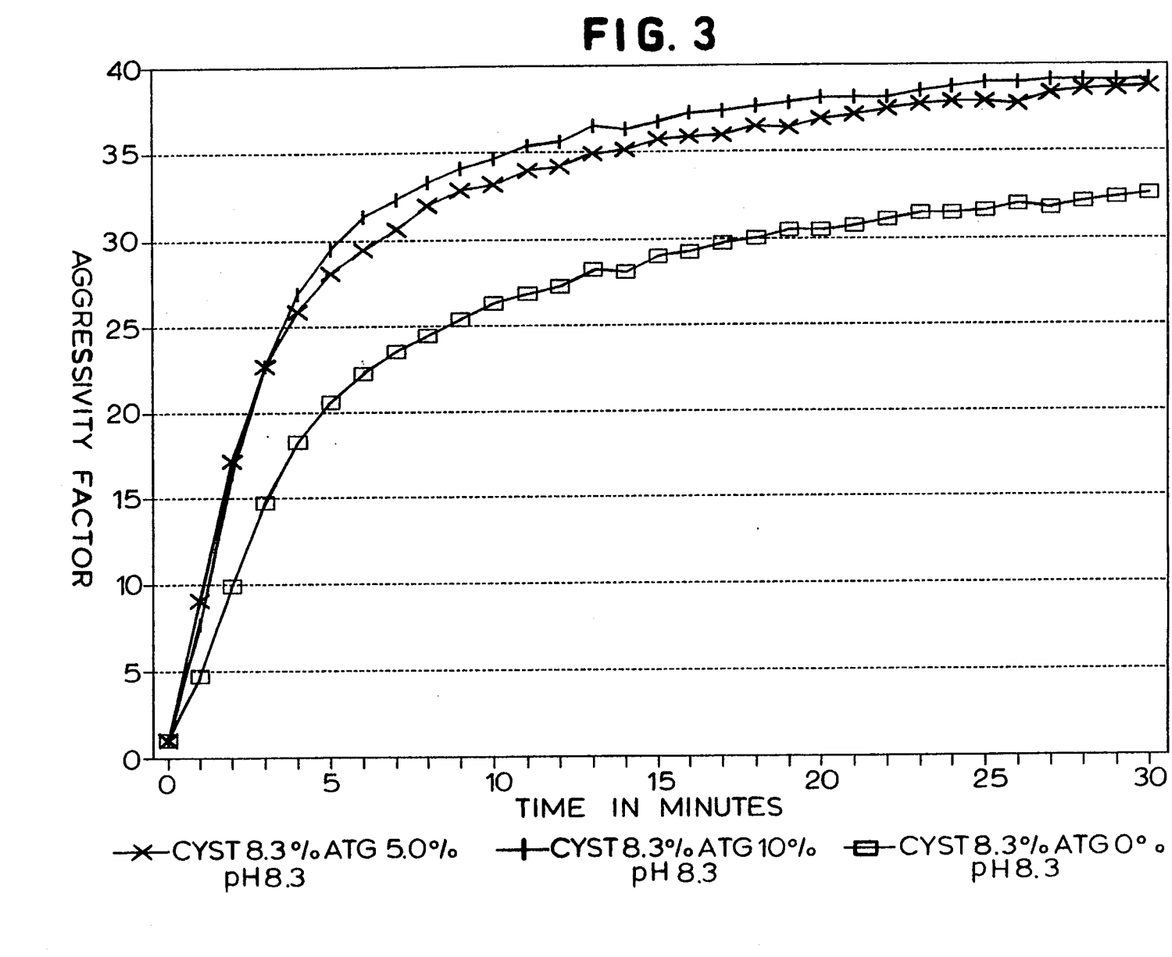
FIG. 3 is a graph showing the activity of a cysteamine-based waving lotion without a second reducing agent, in comparison to a cysteamine-based waving lotion containing a second, monothioglycolate (ATG) reducing agent.

The following data, in Table I and FIG. 3, illustrate the levelling of aggressiveness of the hybrid cysteamine-based waving lotions of the present invention, in comparison to cysteamine as a sole reducing agent.

TABLE I

PERCENT CHANGE IN AGGRESSIVITY FACTOR OVER TIME

| Waving Lotion (weight %) | Reading at 5 mins. | Average Reading Between 25–30 mins. | % Change |
|---|---|---|---|
| 8.3% CYSTEAMINE 5% ATG pH 8.3 | 28.11 | 38.33 | 36.38 |
| 8.3% CYSTEAMINE 10% ATG pH 8.3 | 29.51 | 39.05 | 32.36 |
| 8.3% CYSTEAMINE 0% ATG pH 8.3 | 20.55 | 32.06 | 56.02 |

Figure 4:
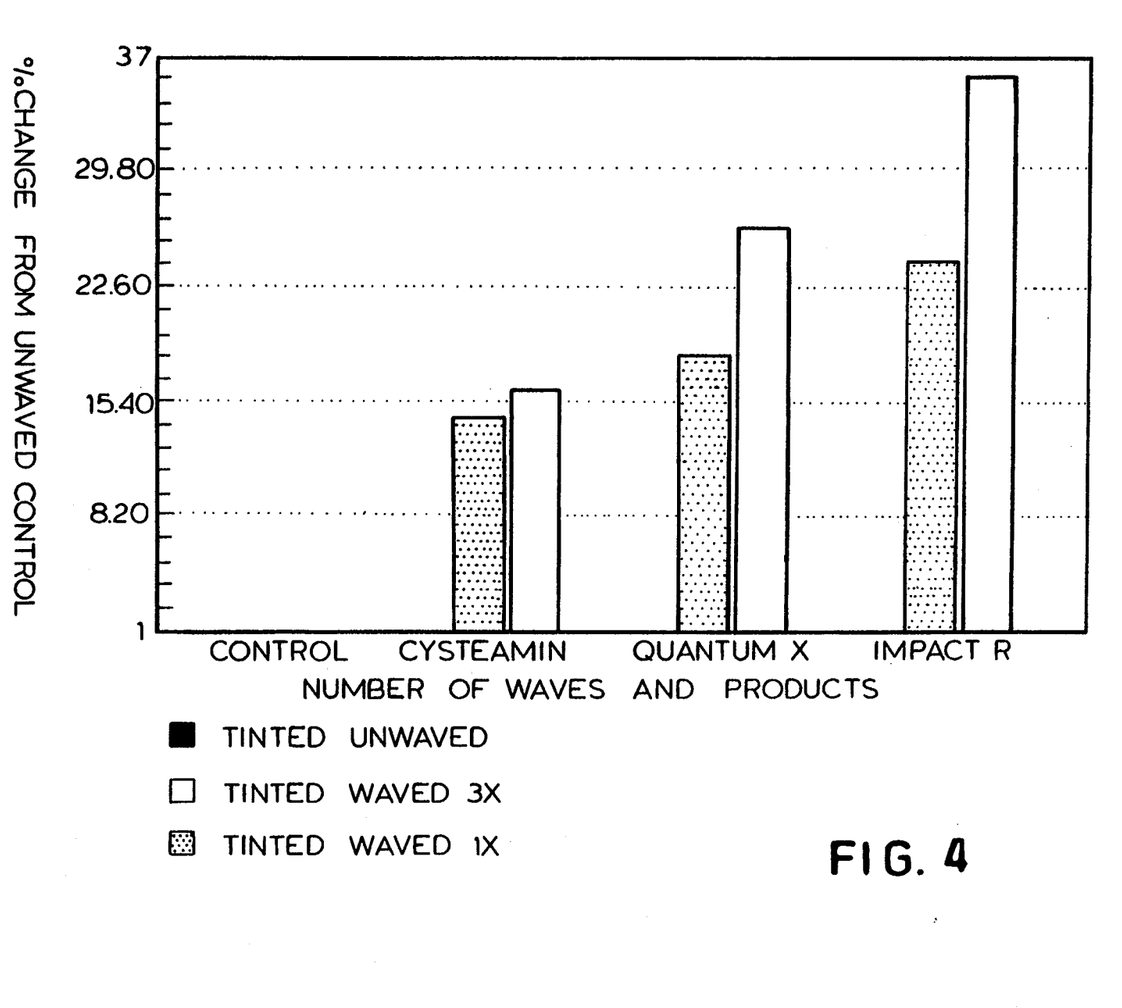
FIG. 4 is a graph showing the change in liquid retention of tinted hair waved one time and three times with acid (GMT), alkaline (ATG) and cysteamine waving lotions.
Figure 5:
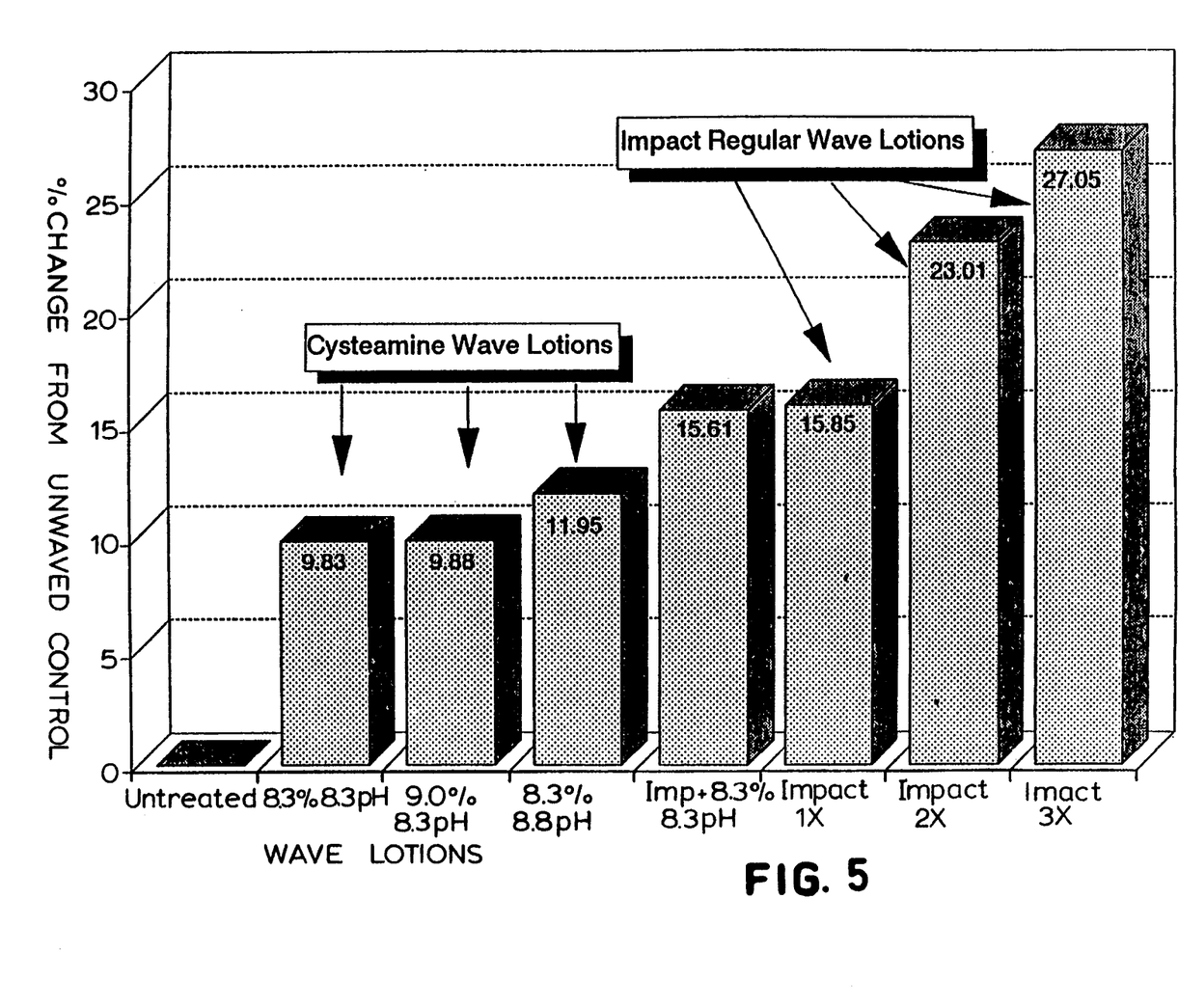
FIG. 5 is a graph showing the change in liquid retention of normal hair waved one, two and three times with an alkaline (ATG) waving lotion in comparison to normal hair waved once with cysteamine at different concentrations, and compared to normal hair waved once with the alkaline waving lotion and a second time with cysteamine.

Hair damage can be measured analytically in the laboratory by a technique called Liquid Retention. The principle involved in the Liquid Retention test is based on the fact that damaged hair becomes more porous and absorbs more moisture. The greater the amount of moisture picked up by the hair, the greater the damage. There should be no significant increase in the amount of moisture picked up by hair that is waved one time and three times with a waving lotion containing a combination of cysteamine and a second reducing agent, such as ammonium thioglycolate. However, with the acid and alkaline waved hair, the moisture pick up after three wavings is significantly greater than one time waved hair, as shown in FIGS. 4 and 5.

Figure 1:
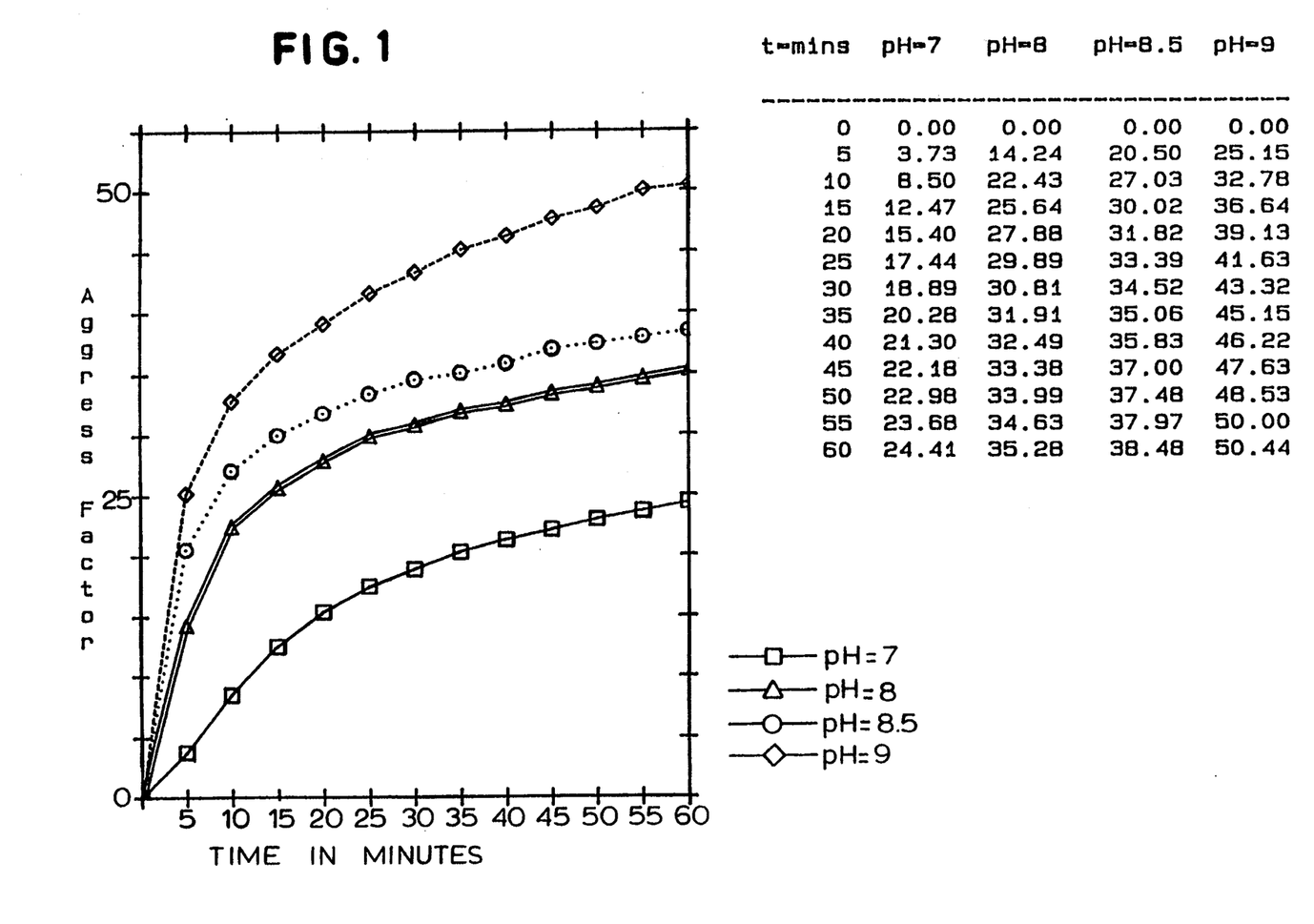
FIG. 1 is a graph showing the activity of ammonium thioglycolate (ATG) versus time.

Hair damage also can be measured using an "Aggressivity factor" test as described in TECHNOLOGIES et SCIENCE en COSMETOLOGIE (COSMETIC TECHNOLOGY and SCIENCE) "PREPRINTS—ORAL COMMUNICATIONS," Volume II, pp. 391-406 (see p. 397), IFSSC Conference, Paris, Sep. 14-17, 1982, hereby incorporated by reference. In the "Aggressivity factor" test, with ATG and glycerylmonothioglycolate (GMT) at a constant concentration, when pH is varied, as shown in FIG. 1 for ATG, the Aggressivity factor increases with time, indicating that the damage done to the hair is progressively worse. Similarly, when the pH is kept constant and the concentration is varied, hair damage gets progressively worse.

With the cysteamine-containing hybrid waving lotions of the present invention, the Aggressivity factor levels off within a relatively narrow cysteamine pH and concentration range and is not as linear as for the second reducing agents used alone. This levelling of the Aggressivity factor indicates that damage to the hair does not get worse when hair is exposed to increasing concentrations or pH of the hybrid waving lotion when cysteamine is included in the waving lotion at a concentration of about 7.8% to about 9% by weight and the pH of the hybrid composition is in the range of about 7.8 to about 8.8.

With ATG and GMT alone, increasing the pH or concentration increases the number of reduced sites on the hair. With cysteamine and a second reducing agent, for example, ammonium thioglycolate, there is substantially little or no change in aggressivity with increased concentration of the second reducing agent, as shown in FIG. 3.

As shown in FIG. 1, when the pH of ATG is raised from 7 to 8 to 8.5 to 9, its aggressivity increases and statistically these curves are significantly different from each other. The concentration of ATG in the waving lotion of FIG. 1 was kept constant at 9%.

Figure 2:
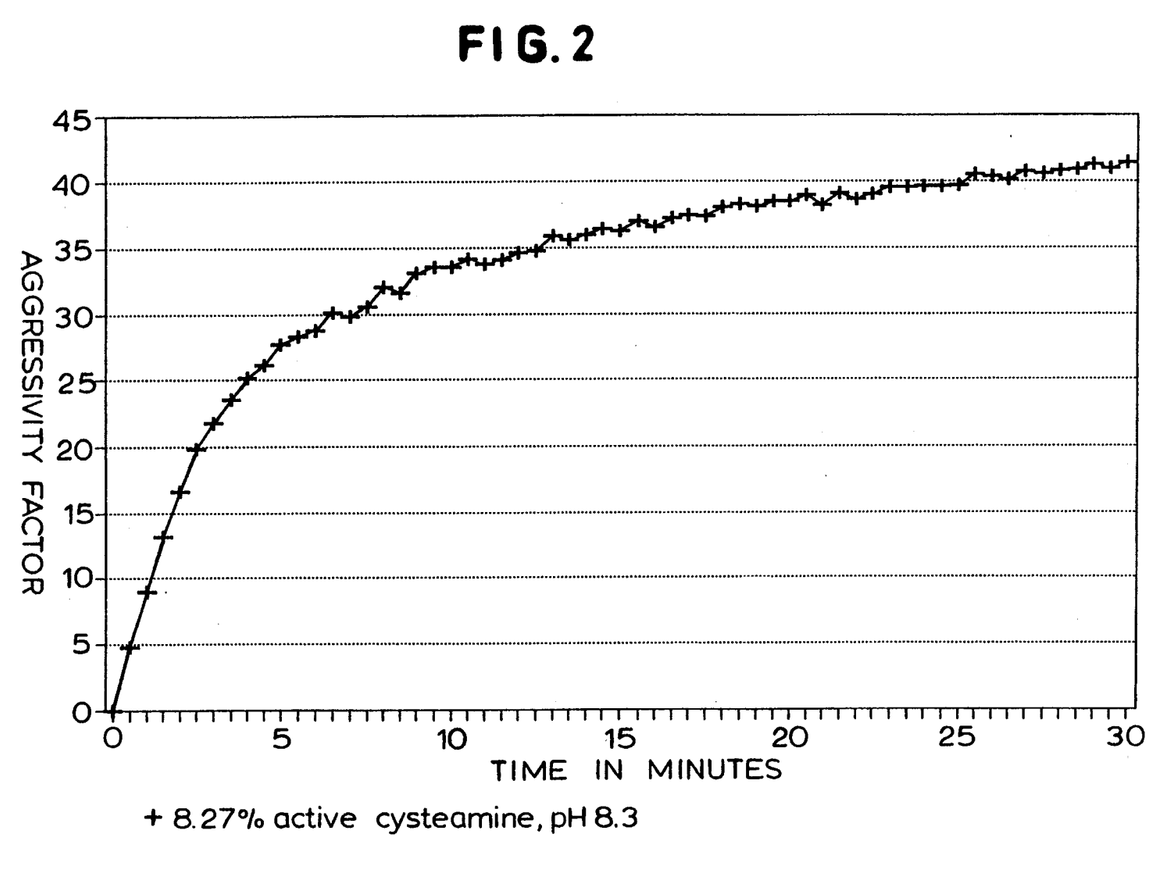
FIG. 2 is a graph showing the activity of cysteamine versus time.

As shown in FIG. 2, cysteamine alone, at a pH of about 8.3 and a concentration of about 8.3% by weight, provides an essentially constant Aggressivity factor, in comparison to ATG. The following Table II also shows that cysteamine alone reaches a maximum (although essentially constant) aggressivity at a concentration of about 8.3% by weight and a pH of about 8.3.

TABLE II

MULTIPLE RANGE ANALYSIS FOR AGGRESSIVENESS FACTOR

| Count | Average Aggressivity | Cysteamine wt. % | pH |
|---|---|---|---|
| 60 | 27.32 | 8.3% | 7.3 pH |
| 60 | 28.68 | 8.3% | 7.8 pH |
| 60 | 29.81 | 7.8% | 8.3 pH |
| 60 | 30.73 | 8% | 8.3 pH |
| 60 | 32.36 | 9.8% | 8.3 pH |
| 60 | 32.60 | 9% | 8.3 pH |
| 60 | 33.48 | 8.3% | 8.8 pH |
| 60 | 33.81 | 8.3% | 8.3 pH |

As shown in FIG. 3, a hybrid waving lotion containing both ATG and cysteamine has an activity (Aggressivity factor) that is essentially constant with time, like that of cysteamine alone, but has an increased aggressivity for better curl formation. As shown in FIG. 3, the increase in aggressivity in a hybrid waving lotion containing 10% ATG, compared to a hybrid waving lotion containing 5% ATG, is not substantial. Therefore, low concentrations, e.g., about 1% to about 6% by weight ATG, together with cysteamine at about 7.8% to about 9% by weight, and at a waving lotion pH of about 7.8 to about 8.8, provides a waving lotion having an aggressivity that is essential constant after about 5 minutes of contact time, e.g., 5-30 minutes or more, while providing excellent waving efficiency (tight curl formation). Similarly, within cysteamine molar concentrations of 0.60 to 0.80, the waving efficiencies of cysteamine, together with a second reducing agent, are essentially constant and do not significantly increase.

As shown in FIG. 3, a substantial increase in cysteamine aggressivity is obtained by including a relatively small concentration of a second reducing agent, such as ammonium thioglycolate. It is expected that the hybrid waving lotions of the present invention will be capable of providing repeated permanent waves without substantial increase in hair damage, as shown for cysteamine alone in FIGS. 4 and 5, in comparison to ATG alone (IMPACT R), and GMT alone (QUANTUM X) in FIG. 4; and in comparison to ATG alone in FIG. 5.

FIG. 5 shows the damage caused by a waving lotion containing cysteamine as the only reducing agent on normal (undamaged) hair and previously permed hair in comparison to damage caused by a conventional alkaline (ATG-containing) waving lotion (IMPACT® waving lotion). As shown in the first three bars of the graph, the cysteamine-containing composition, used once, caused relatively little damage to normal (undamaged) hair over varying pHs and concentrations within the specified ranges, in comparison with IMPACT® waving lotion used one time (4th bar). The fourth and fifth bars of FIG. 5 show that the damage to hair waved once with IMPACT® waving lotion and then a second time with a cysteamine waving lotion is essentially the same as the damage caused by a single perm with IMPACT® waving lotion (the second perming with the cysteamine waving lotion caused essentially no additional damage). The last two bars of FIG. 5 show the extensive additional damage caused by a second and third perming with IMPACT® waving lotion, respectively, that is found in repeated perms with all other known, comparable commercially-available waving lotions.

These unexpected findings, with cysteamine and a second reducing agent, namely, constant performance over a relatively narrow pH and concentration range, led to the discovery of further benefits for multiple reducing agent cysteamine-based waving lotions. With conventional waving agents, it is well known in the art to change the concentration and/or pH when waving hair with different degrees of damage. For example, when preparing a formula for bleached hair, formulators will lower the aggressiveness of the active ingredient by lowering its pH or concentration. Since the performance of cysteamine, together with a second reducing agent, does not change over the above-described narrow pH and concentration range, a single composition having the same formula (without changing concentration or pH) can be used to permanently wave normal hair (relatively undamaged), bleached hair, tinted hair, frosted hair and other damaged hair. Accordingly, the hybrid waving lotion of the present invention, containing widely varying amounts of a second reducing agent, such as ammonium thioglycolate, will wave normal, tinted and bleached hair without causing excessive damage to tinted or bleached hair.

Further, hair can be repeatedly permed with a waving lotion containing cysteamine and a second reducing agent in accordance with the principles of the present invention.

Without being bound to any particular theory, cysteamine, within the concentration and pH ranges shown below, has some unexpected properties, namely, minimal damage and good curl efficacy. This may be attributed to the amine functionality of the molecule.

| FORMULATION | % W/W |
|---|---|
| Cysteamine HCl | 7.8–9, preferably 8.3 |
| Ammonium Hydroxide | q.s. to pH 7.8–8.8, preferably 8.3 |
| Ammonium Thioglycolate | 0.1–18%, preferably 2–6% |
| Nonoxynol-15 (Igepal CO-730) (fragrance solubilizer) | 0.90 |
| Fragrance | 0.30 |
| Water | q.s. to 100 |

Actual waving lotion compositions, having a preferred pH of 8.3 were prepared using the above formula including 0%, 5% and 10% ATG, together with 8.3% by weight cysteamine, as shown in FIG. 3.

The invention described herein is a further improvement in that the curl formation is increased by the addition of a second reducing agent while, at the same time, maintaining the other benefits of the cysteamine reducing agent.

It has been found that the aggressivity of cysteamine wave lotions can be increased by the addition of a second reducing agent, such as ammonium thioglycolate (see FIG. 3). One unexpected finding is that the aggressivity increases to the essentially same extent regardless of the amount of second reducing agent, e.g., ammonium thioglycolate, that is added to the cysteamine-based waving lotion. Another surprising finding is that in hybrid formulations, the aggressivity levels off even faster than when cysteamine was used alone. As shown by the data in Table I, the hybrid waving lotion approaches its essentially constant aggressivity faster than when using cysteamine alone (see reading at 5 minutes versus reading at 25–30 minutes or % change), making the time of waving lotion contact with the hair even less critical than for cysteamine alone.

The hybrid, multiple reducing agent containing waving lotions of the present invention represent an improvement over cysteamine formulations without a second reducing agent, such as ammonium thioglycolate, since the hybrid waving lotions maintain all the advantages of cysteamine at a higher curl performance level, with even less criticality in processing time.

Many modifications and variations of the invention as hereinbefore set forth can be made without departing from the spirit and scope thereof and, therefore, only such limitations should be imposed as are indicated by the appended claims.

What is claimed is:

1. A permanent wave composition capable of breaking sulfur to sulfur bonds in human hair when in contact with said human hair so that said hair can be reconfigured in a predetermined configuration, comprising an aqueous solution of a cysteamine in an amount of about 7.8% to about 9% by weight of the permanent wave composition; sufficient alkali such that the composition has a pH of about 7.8 to about 8.8, and a second reducing agent in an amount of about 0.1 to about 18% by weight of the waving composition.

2. The composition of claim 1, wherein the second reducing agent is selected from the group consisting of a monothioglycolate; an alkanolamine salt of thioglycolic acid; a thiolactic acid; a thioglycolic acid; thioglycerin; salts of thiolactic acid; cysteine; a salt of cysteine; a sulfite; a hyposulfite; and a bisulfite.

3. The composition of claim 2, wherein the second reducing agent is a monothioglycolate.

4. The composition of claim 3, wherein the monothioglycolate is selected from the group consisting of ammonium thioglycolate, potassium thioglycolate, sodium thioglycolate, and mixtures thereof.

5. The composition of claim 4, wherein the monothioglycolate is ammonium thioglycolate.

6. The composition of claim 1 further including a polyhydric moisturizer selected from the group consisting of polyhydroxyalkyl compounds; polyalkylene glycols; glyceryl ether compounds; ethoxylated fatty alcohols; ethoxylated alkyl phenols; fatty alcohol polyglycol ether compounds; and mixtures thereof.

7. The composition of claim 1, wherein the cysteamine is included in an amount of about 7.8% to about 8.7% by weight of the composition.

8. The composition of claim 7, wherein the cysteamine is cysteamine hydrochloride.

9. The composition of claim 6, wherein the moisturizer is glycerine or a polyalkylene glycol ether of glycerine having an average ethoxylation value of 5 to 50.

10. The composition of claim 1 further including a quaternary ammonium conditioning compound in an amount of about 0.1% to about 2% by weight of the composition.

11. The composition of claim 1, wherein the cysteamine is included in the composition in a concentration of about 0.60 to about 0.80 molar.

* * * * *

UNITED STATES PATENT AND TRADEMARK OFFICE
CERTIFICATE OF CORRECTION

PATENT NO. : 5,362,487
DATED : NOVEMBER 8, 1994
INVENTORS : NANDAGIRI ET AL.

It is certified that error appears in the above-identified patent and that said Letters Patent is hereby corrected as shown below:

Column 9, line 13, after "such as" delete "bentonire" and substitute therefor -- bentonite --;

Column 11, line 5, after "described in" delete "TECHNOLOGIES" and substitute therefor -- TECHNOLOGIE --;

Column 11, line 10, delete "14" and substitute therefor -- 13; and

Column 13, before the table insert the following: -- The preferred composition is as follows: --.

Signed and Sealed this

Twenty-eight Day of February, 1995

*Attest:*

BRUCE LEHMAN

*Attesting Officer*     *Commissioner of Patents and Trademarks*